US010312464B2

(12) United States Patent
Rothe et al.

(10) Patent No.: US 10,312,464 B2
(45) Date of Patent: Jun. 4, 2019

(54) ACTIVE OLED DISPLAY, METHOD OF OPERATING AN ACTIVE OLED DISPLAY AND COMPOUND

(71) Applicant: Novaled GmbH, Dresden (DE)

(72) Inventors: Carsten Rothe, Dresden (DE); Thomas Rosenow, Dresden (DE); Martin Koehler, Dresden (DE); Mike Zoellner, Bergisch Gladbach (DE); Andreas Haldi, Heidelberg (DE); Tobias Canzler, Dresden (DE)

(73) Assignee: Novaled GmbH, Dresden (DE)

( * ) Notice: Subject to any disclaimer, the term of this patent is extended or adjusted under 35 U.S.C. 154(b) by 19 days.

(21) Appl. No.: 15/515,174

(22) PCT Filed: Sep. 30, 2015

(86) PCT No.: PCT/EP2015/072539
§ 371 (c)(1),
(2) Date: Mar. 29, 2017

(87) PCT Pub. No.: WO2016/050834
PCT Pub. Date: Apr. 7, 2016

(65) Prior Publication Data
US 2017/0222170 A1  Aug. 3, 2017

(30) Foreign Application Priority Data
Sep. 30, 2014  (EP) ..................................... 14187061

(51) Int. Cl.
*H01L 29/08* (2006.01)
*H01L 51/50* (2006.01)
(Continued)

(52) U.S. Cl.
CPC .......... *H01L 51/506* (2013.01); *C07C 211/56* (2013.01); *H01L 27/3211* (2013.01); *H01L 51/0059* (2013.01)

(58) Field of Classification Search
CPC ...................................................... H01L 51/506
(Continued)

(56) References Cited

U.S. PATENT DOCUMENTS

2005/0110009 A1† 5/2005 Blochwitz-Nimoth
2010/0288362 A1† 11/2010 Hatwar
(Continued)

FOREIGN PATENT DOCUMENTS

| WO | 2010/011368 A1 | 1/2010 |
| WO | 2011/134458 A1 | 11/2011 |
| WO | 14129201 A1 † | 8/2014 |

OTHER PUBLICATIONS

Chinese Office Action for CN Application No. 201580053032.0 dated Apr. 4, 2018 (8 pages) (English translation).
(Continued)

*Primary Examiner* — Caleb E Henry
(74) *Attorney, Agent, or Firm* — Eversheds Sutherland (US) LLP

(57) ABSTRACT

An active OLED display, comprising a plurality of OLED pixels, each of the OLED pixels comprising an anode, a cathode, and a stack of organic layers, wherein the stack of organic layers is provided between and in contact with the cathode and the anode and comprises an electron transport layer, a hole transport layer, and a light emitting layer provided between the hole transport layer and the electron transport layer, and a driving circuit configured to separately driving the pixels of the plurality of OLED pixels, wherein, for the plurality of OLED pixels, a common hole transport layer is formed by the hole transport layers provided in the stack of organic layers of the plurality of OLED pixels, the common hole transport layer comprising a hole transport matrix material and at least one electrical p-dopant, and the
(Continued)

Figure 1:
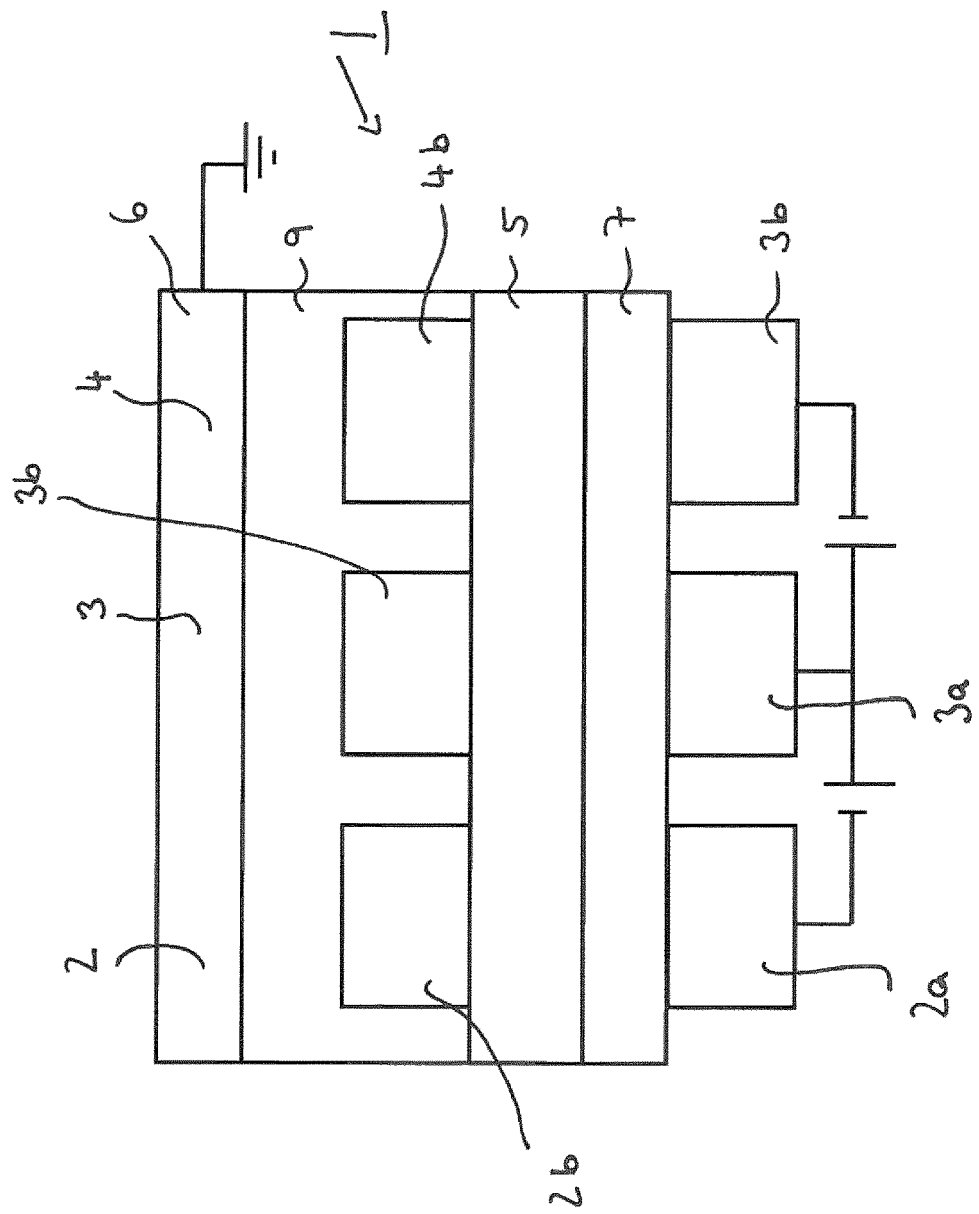

electrical conductivity of the hole transport material being lower than $1 \times 10^{-3}$ S·m$^{-1}$ and higher than $1 \times 10^{-8}$ S·m$^{-1}$.

17 Claims, 3 Drawing Sheets

(51) Int. Cl.
*H01L 51/00* (2006.01)
*H01L 27/32* (2006.01)
*C07C 211/56* (2006.01)

(58) Field of Classification Search
USPC .......................................................... 257/40
See application file for complete search history.

(56) References Cited

U.S. PATENT DOCUMENTS

| | | | | |
|---|---|---|---|---|
| 2012/0138904 | A1* | 6/2012 | Shimizu | H01L 51/0004 257/40 |
| 2012/0235144 | A1* | 9/2012 | Choung | H01L 51/5231 257/57 |
| 2013/0048954 | A1† | 2/2013 | Lee | |
| 2014/0264295 | A1 | 9/2014 | Sim et al. | |
| 2015/0011795 | A1 | 1/2015 | Zoellner et al. | |
| 2016/0021718 | A1* | 1/2016 | Kikuchi | H01L 51/5271 362/231 |
| 2016/0300898 | A1* | 10/2016 | Kim | H01L 27/3262 |

OTHER PUBLICATIONS

European Search Report for EP Application No. 14 18 7061 dated Mar. 9, 2015 (2 pages).

PCT International Search Report and Written Opinion for PCT Application No. PCT/EP2015/072539 dated Dec. 11, 2015 (11 pages).

\* cited by examiner
† cited by third party

ACTIVE OLED DISPLAY, METHOD OF OPERATING AN ACTIVE OLED DISPLAY AND COMPOUND

CROSS REFERENCE TO RELATED APPLICATIONS

This application is a U.S. national stage application of PCT/EP2015/072539, filed Sep. 30, 2015, which claims priority to European Application No. 14187061.8, filed Sep. 30, 2014. The contents of these applications are hereby incorporated by reference.

The disclosure relates to an active OLED display having a plurality of OLED pixels, a method of operating an active OLED display and a compound.

BACKGROUND

Since 1987, when low operating voltages have been demonstrated by Tang et al. (C. W. Tang et al. Appl. Phys. Lett. 51 (12) 913 (1987)), organic light-emitting diodes have been promising candidates for the realization of large-area displays. They consist of a sequence of thin (typically 1 nm to 1 μm) layers of organic materials, which can be deposited, for example, by thermal vacuum evaporation or solution processing, followed by formation of the electrical contacts through metallic layers. Organic electrical devices offer a great variety of electronic or optoelectronic components, such as diodes, light-emitting diodes, photodiodes and thin film transistors (TFT), which, in terms of properties, compete with established components based on inorganic materials.

In the case of organic light-emitting diodes (OLEDs), light is produced and emitted by the light-emitting diode through the injection of charge carriers (electrons from one side, holes from another side) from the contacts into adjacent organic layers as a result of an externally applied voltage, subsequent formation of excitons (electron-hole pairs) in an active zone, and radiative recombination of these excitons.

The advantage of such organic components over conventional inorganic components (based on inorganic semiconductors such as silicon or gallium arsenide) is the option to produce large-area elements, e.g. large display elements (visual displays, screens) or lamps (for lighting applications). Organic materials, compared to inorganic materials, are relatively inexpensive (less expenditure of material and energy). Moreover, these materials, because of their low processing temperature compared to inorganic materials, can be deposited on flexible substrates, thereby opening up a whole series of new applications in display and illuminating engineering.

The basic construction of such a component includes an arrangement of one or more of the following layers: Carrier substrate; hole-injecting (positive contact) base electrode which is usually transparent; hole-injecting layer (HIL); hole-transporting layer (HTL); light-emitting layer (EL); electron-transporting layer (ETL); electron-injecting layer (EIL); electron-injecting (negative contact) cover electrode, usually a metal with low work function; and encapsulation, to exclude ambient influences.

While the foregoing represents the most typical case, often several layers may be (with the exception of HTL and ETL) omitted, or else one layer may combine several properties.

The use of doped charge-carrier transport layers (p-doping of the HTL by admixture of acceptor-like molecules, n-doping of the ETL by admixture of donor-like molecules) is described in document U.S. Pat. No. 5,093,698. Doping in this sense means that the admixture of doping substances into the layer increases the equilibrium charge-carrier concentration in this layer, compared to the pure layers of one of the two substances concerned, which results in improved electrical conductivity and better charge-carrier injection from the adjacent contact layers into this mixed layer. The transport of charge carriers still takes place on the matrix molecules. According to U.S. Pat. No. 5,093,698, the doped layers are used as injection layers at the interface to the contact materials, the light-emitting layer being found in between (or, when only one doped layer is used, next to the other contact). Equilibrium charge-carrier density, increased by doping, and associated band bending, facilitate charge-carrier injection. The energy levels of the organic layers (HOMO=highest occupied molecular orbital or highest energetic valence band energy; LUMO=lowest unoccupied molecular orbital or lowest energetic conduction band energy), according to U.S. Pat. No. 5,093,698, should be obtained so that electrons in the ETL as well as holes in the HTL can be injected into the EL (emitting layer) without further barriers, which requires very high ionization energy of the HTL material and very low electron affinity of the ETL material.

With respect to active OLED displays, so-called crosstalk between pixels of the display has been a major problem. Pixel or colour crosstalk refers to photons of one colour generated by a pixel falsely mixing with photons of another colour scattered from a close pixel. For example, documents GB 2 492 400 A and WO 2002/015292 A2 provide measures for reducing colour crosstalk in OLED devices. In addition, or as an alternative aspect, electrical crosstalk may occur. In this case, for example, a driving current applied to one of the pixels may cause light emission from another pixel close to the pixel for which the driving current is provided. Both will have a negative impact on the performance of the display device. (see Yamazaki et al., A. (2013), 33.2: Spatial Resolution Characteristics of Organic Light-emitting Diode Displays: A comparative Analysis of MTF for Handheld and Workstation Formats. SID Symposium Digest of Technical Papers, 44: 419-422. doi: 10.1002/j.2168-0159.2013.tb06236.x).

In a typical commercial active matrix OLED display, electrical pixel cross talk may be caused by the application of redox p-doping in a hole transport layer (HTL) which is shared by more OLED pixels (in the sense that the shared HTL is electrically connected to anodes of a plurality of pixels present in the display). The use of redox p-dopants which increase charge carrier density by creation of new charge carriers (holes) by transfer of an electron from a molecule of the doped matrix to a dopant molecule is beneficial for low-operating voltage, high operational stability and high production yield. On the other hand, redox p-doping increases electrical conductivity of hole transport layers from less than $10^{-8}$ S/cm without p-dopant, usually from less than $10^{-10}$ S/cm, to more than $10^{-6}$ S/cm (typically, with concentrations of the p-dopant in the range between 1 and 5 wt. %). Therefore, redox-doped HTL is usually responsible for any electrical pixel cross talk in active matrix displays comprising a HTL shared by plurality of pixels. The ETL, if n-doped with redox n-dopants, might also show similarly high conductivity as the redox-doped HTL, however, due to display layout with a common cathode, the ETL does not cause electrical pixel cross talk.

SUMMARY

It is an object to provide improved technologies for active OLED displays, in particular, cross talk between neighbor pixels of the active OLED display shall be reduced.

In one aspect, an active OLED display is provided. In some embodiments, the active OLED display includes a plurality of OLED pixels, each of the OLED pixels comprising an anode, a cathode, and a stack of organic layers, wherein the stack of organic layers is provided between and in contact with the cathode and the anode, and comprises an electron transport layer, a hole transport layer, and a light emitting layer provided between the hole transport layer and the electron transport layer, and a driving circuit configured to separately driving the pixels of the plurality of OLED pixels, wherein, for the plurality of OLED pixels, a common hole transport layer is formed by the hole transport layers provided in the stack of organic layers of the plurality of OLED pixels, the common hole transport layer comprising a hole transport matrix material and an electrical p-dopant, and wherein the electrical conductivity of the common hole transport layer is lower than $1 \times 10^{-3}$ S·m$^{-1}$ and higher than $1 \times 10^{-8}$ S·m$^{-1}$. In another aspect, methods of operating an active OLED display are provided. In some embodiments, the methods include operating an active OLED display having a plurality of OLED pixels as provided herein, wherein a driving circuit applies a driving current to each pixel of the plurality of OLED pixels, the driving current being different for neighbor OLED pixels at an operation time. In a still further aspect, compounds are provided. In some embodimensts the compounds have the following formula:

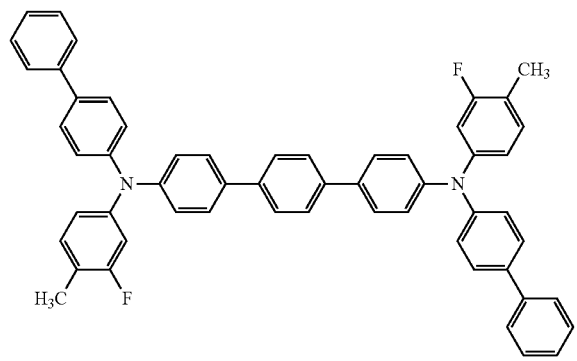 [SMILES: Cc1ccc(N(c2ccc(-c3ccccc3)cc2)c2ccc(-c3ccc(-c4ccc(N(c5ccc(-c6ccccc6)cc5)c5ccc(C)c(F)c5)cc4)cc3)cc2)cc1F]

In one aspect, an active OLED display having a plurality of OLED pixels is provided. The active OLED display comprises a plurality of OLED pixels, wherein each of the OLED pixels comprises an anode, a cathode, and a stack of organic layers. The stack of organic layers is provided between and in contact with the cathode and the anode and comprises an electron transport layer, a hole transport layer, and a light emitting layer provided between the hole transport layer and the electron transport layer. The contact between the stack of organic layers and the cathode as well as with the anode may be an electrical contact. Further, the active OLED display comprises a driving circuit configured to separately driving the pixels of the plurality of OLED pixels. For the plurality of OLED pixels, a common hole transport layer is formed by the hole transport layers provided in the stack of organic layers of the plurality of OLED pixels. The common hole transport layer comprises a hole transport matrix material and an electrical p-dopant. The electrical conductivity of the common hole transport layer may be lower than $1 \times 10^{-3}$ S·m$^{-1}$ and higher than $1 \times 10^{-8}$ S·m$^{-1}$. The electrical conductivity of the common hole transport layer refers to the electrical conductivity of the hole transport matrix material doped with the electrical p-dopant. Alternatively or in addition to the range of the electrical conductivity of the common hole transport layer, a hole mobility of the hole transport matrix material may be lower than $5 \times 10^{-4}$ cm$^2$/Vs. Electrical crosstalk between the OLED pixels may be limited or even eliminated for the active OLED display proposed.

An important property of organic semi-conducting devices is their conductivity. By electrical doping, the electrical conductivity of a layer of an organic semi-conducting device can be significantly increased. The electrical conductivity of a thin layer sample can be measured by, for example, the so called two-point method. At this, a voltage is applied to the thin layer and the current flowing through the layer is measured. The resistance, respectively the electrical conductivity, results by considering the geometry of the contacts and the thickness of the layer of the sample.

Charge carrier mobility in an organic layer can be determined from capacitance vs. frequency traces obtained by means of admittance spectroscopy (see, for example, Nguyen et al., Determination of charge-carrier transport in organic devices by admittance spectroscopy: Application to hole mobility in α-NPD." Physical Review B 75.7 (2007): 075307).

In another aspect, a method of operating an active OLED display having a plurality of OLED pixels is provided. A driving circuit applies a driving current to each pixel of the plurality of OLED pixels, wherein the driving current is different for neighbor OLED pixels at an operation time. At least at one point during operation of the OLED display, different electrical potentials are applied to neighbor pixels.

In still another aspect, a compound having formula

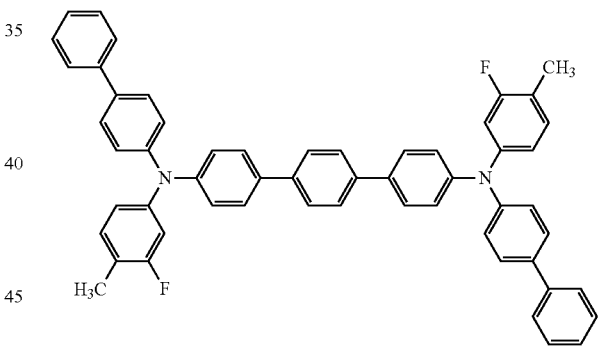

is disclosed.

Optionally, for one or more of the plurality of OLED pixels, following organic layers may be provided: a hole blocking layer, an electron injection layer, and / or an electron blocking layer.

The electrical conductivity of the common hole transport layer may be lower than $5 \times 10^{-4}$ S·m$^{-1}$, lower than $1 \times 10^{-4}$ S·m$^{-1}$, lower than $5 \times 10^{-5}$ S·m$^{-1}$, or lower than $1 \times 10^{-5}$ S·m$^{-1}$. The electrical conductivity of the common hole transport layer may be higher than $5 \times 10^{-8}$ S·m$^{-1}$, higher than $1 \times 10^{-7}$ S·m$^{-1}$, higher than $5 \times 10^{-7}$ S·m$^{-1}$, or higher than $1 \times 10^{-6}$ S·m$^{-1}$.

The common hole transport layer (HTL) may be formed for the plurality of OLED pixels in the OLED display. In one embodiment, the common HTL may extend over all pixels of the plurality of pixels in the OLED display. Similarly, the cathode may be formed as a common cathode for the plurality of pixels. The common cathode may extend over all pixels of the plurality of pixels in the OLED display. Every individual pixel may have its own anode that may not touch anodes of other individual pixels.

Further, the active OLED display has driving circuit configured to separately drive the individual pixels of the plurality of pixels provided in the OLED display. In one embodiment, a step of separately driving may comprise separate control of the driving current applied the individual pixels.

The common HTL is made of a hole transport matrix (HTM) material electrically doped with a p-dopant. The hole transport matrix material may be electrically doped with more than one p-dopant. It is to be understood that the HTM material consists of one or more HTM compounds, whereas the term hole transport material is a broader term used throughout this application for all semiconducting materials comprising at least one HTM compound. The hole transport matrix material may consist of one or more organic compounds.

The LUMO energy level of the electrical p-dopant, expressed in the absolute scale referring to vacuum energy level being zero, may be at least 150 meV, at least 200 meV, at least 250 meV, at least 300 meV, or at least 350 meV higher than the highest HOMO energy level of the compounds forming the HTM material.

The LUMO energy level of the electrical p-dopant, expressed in the absolute scale referring to vacuum energy level being zero, may be less than 600 meV, less than 550 meV, less than 500 meV, less than 450 meV, or less than 400 meV above the highest HOMO energy level of the compounds forming the HTM material.

The HTM may consist of compounds having energies of their highest occupied molecular orbitals, expressed in the absolute scale referring to vacuum energy level being zero, in the range from −4.8 to −5.5 eV, from −4.9 to −5.4 eV, or from −5.0 to −5.3 eV.

The common hole transport layer may have a thickness of less than 50 nm, less than 40 nm, less than 30 nm, less than 20 nm, or less than 15 nm.

The common hole transport layer may have a thickness of more than 3 nm, more than 5 nm, more than 8 nm, or more than 10 nm.

The anode may be made of a transparent conductive oxide (TCO), like indium tin oxide (ITO). Alternatively, the anode may be made of one or more thin metallic layers leading to a semitransparent anode. In another embodiment, the anode may be made of a thick metallic layer which is not transparent to visible light.

In one embodiment, the work function of the anode, expressed in the absolute scale referring to vacuum energy level being zero, may be less than 500 meV, less than 450 meV, less than 400 meV, less than 350 meV, or less than 300 meV above the highest LUMO energy level of compounds forming the p-dopant in the common HTL.

The OLED pixel(s) may comprise an electron blocking layer (EBL) provided between the hole transport layer and the light emitting layer. The EBL may be in direct contact with the common HTL and the EML. The electron blocking layer may be an electrically non-doped layer (in other words, it may be free of an electrical dopant) made of an organic hole transport matrix material. The composition of the organic hole transport matrix material of the common hole transport layer may be the same as the composition of the organic hole transport matrix material of the electron blocking layer. In another embodiment of the invention, the composition of both hole transport matrix materials may be different.

The EBL may have a layer thickness of more than 30 nm, more than 50 nm, more than 70 nm, more than 100 nm, or more than 110 nm.

The thickness of the EBL may be less than 200 nm, less than 170 nm, less than 140 nm, or less than 130 nm. Compared to the EBL, the common HTL may be thinner by about one order of magnitude.

Each compound forming the electron blocking layer may have a HOMO level, expressed in the absolute scale referring to vacuum energy level being zero, higher than a HOMO level of any compound forming the hole transport matrix material of the common hole transport layer. The organic matrix material of the electron blocking layer may be have a hole mobility which is equal to or higher than the hole mobility of the matrix material of the hole transport layer.

The hole transport matrix (HTM) material of the common HTL and/or of the EBL may be selected from compounds comprising a conjugated system of delocalized electrons, the conjugated system comprising lone electron pairs of at least two tertiary amine nitrogen atoms.

Suitable compounds for the hole transport matrix material of the doped hole transport layer and/or the common hole transport layer may be selected from the known hole transport matrices (HTMs), e.g. from triaryl amine compounds. HTMs for the doped hole transport material may be compounds comprising a conjugated system of delocalized electrons, wherein the conjugated system comprises lone electron pairs of at least two tertiary amine nitrogen atoms. Examples are N4,N4'-di(naphthalen-1-yl)-N4,N4'-diphenyl-[1,1'-biphenyl]-4,4'-diamine (HT1), and N4,N4, N4",N4"-tetra([1,1'-biphenyl]-4-yl)-[1,1':4',1"-terphenyl]-4,4"-diamine (HT4). The synthesis of terphenyldiamine HTMs is described e.g. in WO 2011/134458 A1, US 2012/223296 A1 or WO 2013/135237 A1; 1,3-phenylenediamine matrices are described e.g. in WO 2014/060526 A1. These documents are herein incorporated by reference. Many triaryl amine HTMs are commercially available.

The light emitting layer of the OLED display may comprise a plurality of sub-regions, each of the sub-regions being assigned to one of the pixels from the plurality of pixels. The light emitting layer of an individual pixel, corresponding to a sub-region of the emitting layer of the display, preferably does not touch light emitting layers of neighbor pixels. In the display manufacturing process, the organic layer comprising EMLs of individual pixels may be patterned by known methods, for example, by fine-metal masking (FMM), laser induced thermal imaging (LITI), and/or ink jet printing (IJP) in either top emission, bottom emission or bottom emission micro cavity (see, for example, Chung et al. (2006), 70.1: Invited Paper: Large-Sized Full Color AMOLED TV: Advancements and Issues. SID Symposium Digest of Technical Papers, 37: 1958-1963. doi: 10.1889/1.2451418; Lee et al. (2009), 53.4: Development of 31-Inch Full-HD AMOLED TV Using LTPS-TFT and RGB FMM. SID Symposium Digest of Technical Papers, 40: 802-804. doi: 10.1889/1.3256911). A RGB layout may be provided.

For the plurality of OLED pixels, a common electron transport layer may be formed by the electron transport layers provided in the stack of organic layers of the plurality of OLED pixels.

The common electron transport layer may comprise an organic electron transport matrix (ETM) material. Further, the common electron transport layer may comprise one or more n-dopants—Suitable compounds for the ETM contain aromatic or heteroaromatic structural moieties, as disclosed e.g. in documents EP 1 970 371 A1 or WO 2013/079217 A1.

The cathode can be made of a metal or a metal alloy with a low work function. Transparent cathodes made of a TCO are also well-known in the art.

The stack of organic layers may be made of organic compounds having a molecular weight of less than 2000 g/mol. In an alternative embodiment, the organic compounds may have a molecular weight of less than 1000 g/mol.

DESCRIPTION OF EMBODIMENTS

Figure 2:
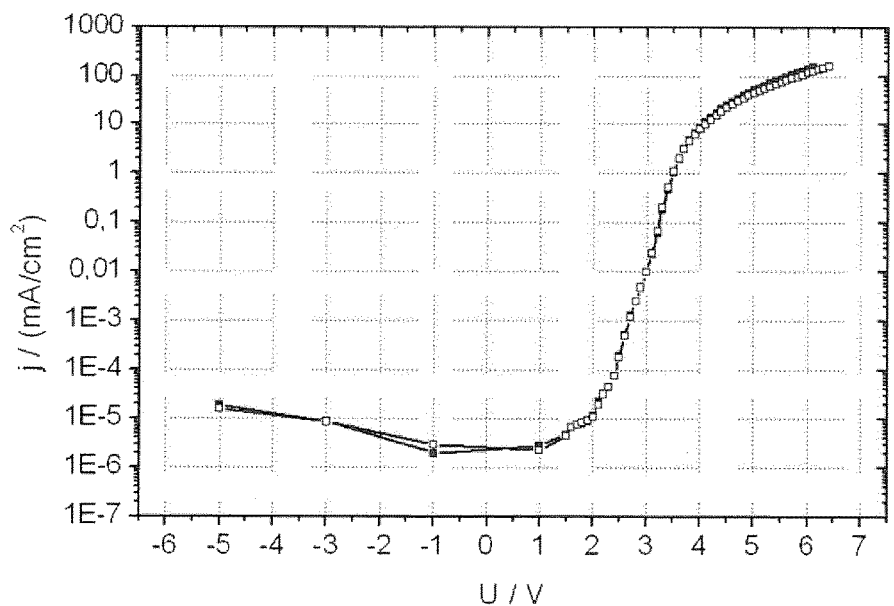
Figure 3:
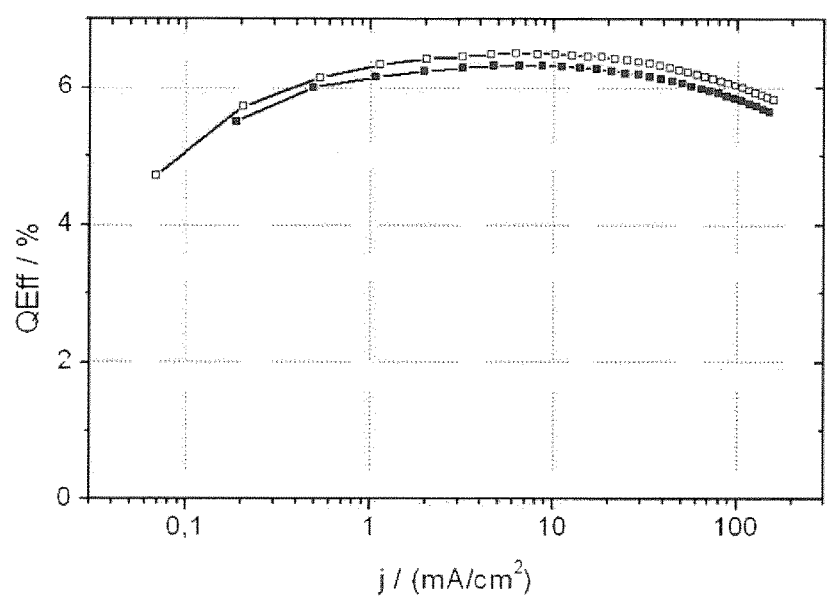
Figure 4:
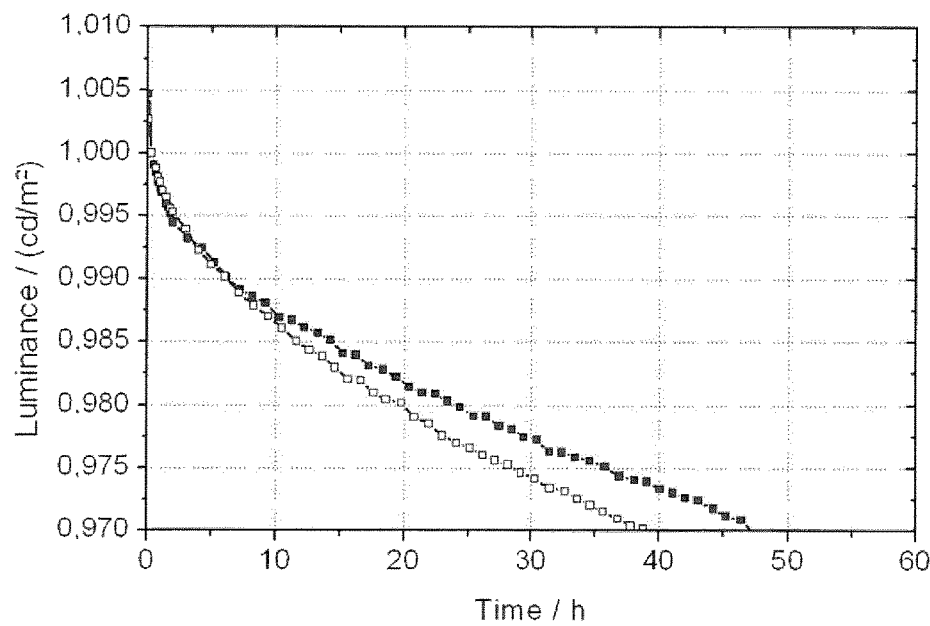
Figure 5:
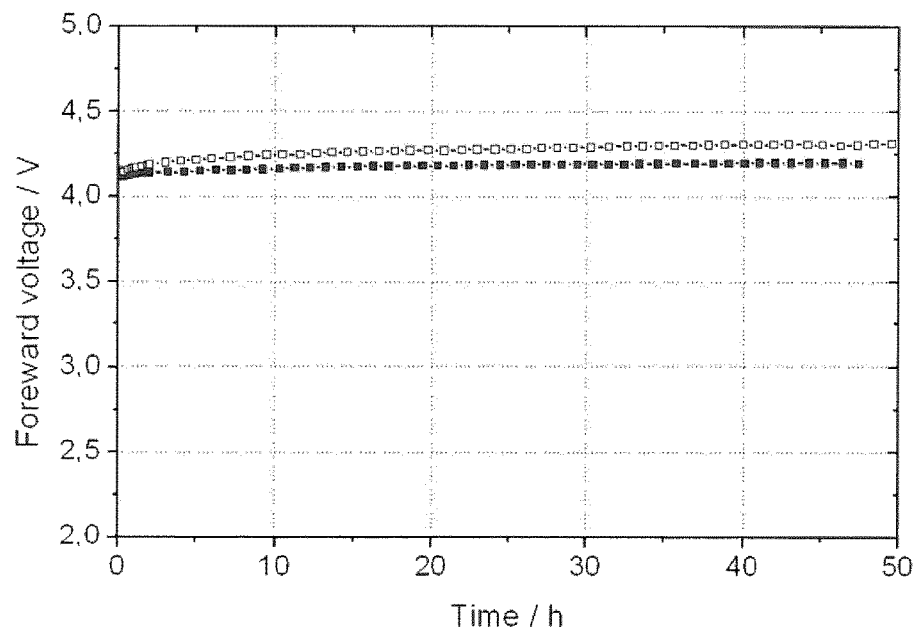

In the following, further embodiments will be described in further detail, by way of example, with reference to figures. In the figures show:

FIG. 1 a schematic representation of an active OLED display, the display having a plurality of OLED pixels, FIG. 2 a graphical representation of the current density vs. voltage for the reference devices of the Comparative example 1 according line 1 of the Table 2 (solid squares) and for the devices according to line 2 of the Table 2 (open squares), respectively;

FIG. 3 a graphical representation of the quantum efficiency vs. current density for the reference devices of the Comparative example 1 according line 1 of the Table 2 (solid squares) and for the devices according to line 2 of the Table 2 (open squares), respectively;

FIG. 4 a graphical representation of the luminance vs. time for the reference devices of the Comparative example 1 according line 1 of the Table 2 (solid squares) and for the devices according to line 2 of the Table 2 (open squares), respectively; and FIG. 5 a graphical representation of the forward voltage vs. time for the reference devices of the Comparative example 1 according line 1 of the Table 2 (solid squares) and for the devices according to line 2 of the Table 2 (open squares), respectively.

FIG. 1 shows a schematic representation of an active OLED display 1 having a plurality of OLED pixels 2, 3, 4 provided in an OLED display 1. In the OLED display 1, each pixel 2, 3, 4 is provided with an anode 2a, 3a, 4a being connected to a driving circuit (not shown). Various equipment able to serve as a driving circuit for an active matrix display is known in the art. In one embodiment, the anodes 2a, 3a, 4a are made of a TCO, for example of ITO.

A cathode 6 is provided on top of an organic stack comprising an electrically doped hole transport layer (HTL) 7, an electron blocking layer (EBL) 5, a light emitting layer (EML) having sub-regions 2b, 3b, 4b assigned to the pixels 2, 3, 4 and being provided separately in an electron transport layer (ETL) 9. For example, the sub-regions 2b, 3b, 4b can provide an RGB combination for a color display (R—red, G—green, B—blue). By applying individual drive currents to the pixels 2, 3, 4 via the anodes 2a, 3a, 4a and the cathode 6, the display pixels 2, 3, 4 are operated independently.

SYNTHESIS EXAMPLES

Synthesis of HT3

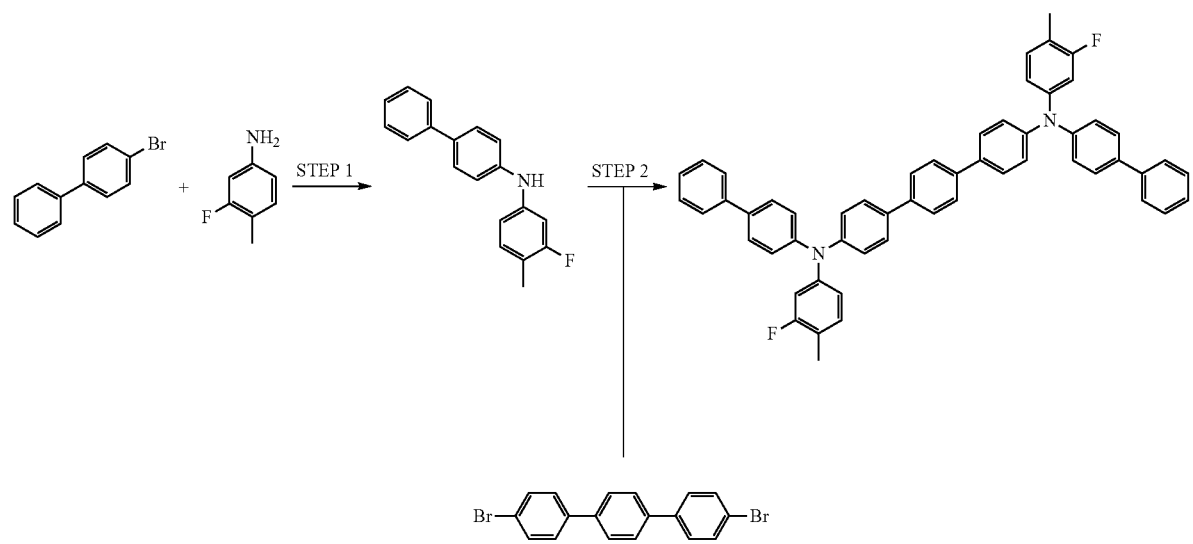

Step 1: Synthesis of N-(3-fluoro-4-methylphenyl)[1,1'-biphenyl]-4-amine

4-Bromobiphenyl (20.0 g, 85.8 mmol), 3-fluoro-4-methylaniline (11.3 g, 90.1 mmol), Pd(OAc)$_2$ (578 mg, 2.57 mmol, 3 mol. %), 2,2'-bis(diphenylphosphino)-1,1'-binaphtalene ((BINAP) 2.40 g, 3.86 mmol, 4.5 mol. %), and Cs$_2$CO$_3$ (39.13 g, 0.12 mol, 1.4 eq.), were charged in a flask under nitrogen atmosphere. The solids were suspended in anhydrous 1,4-dioxane, and the suspension was refluxed for 22 h at 125° C. After cooling to room temperature, it was filtered over silica and the pad was rinsed with dichloromethane. The filtrate was evaporated to dryness and purified by chromatography (silica, elution with hexane/dichloromethane 2:1, R$_f$ in the corresponding TLC system 0.35). The product was isolated in two main fractions: (−1) 7.55 g (32% yield) with 99.73% purity according to HPLC; (−2) 3.75 g (16% yield) with 99.33% purity according to HPLC. Both fractions were mixed together for the next step.

$^1$H NMR (CD$_2$Cl$_2$, 400 MHz): 7.58 (2H, dd, J=8.24 and 1.10 Hz), 7.54 (2H; m-AB; J=8.57 Hz), 7.43 (2H, t, J=7.75 Hz), 7.31 (2H, t, J=7.38 Hz), 7.14 (2H; m-AB; J=8.57 Hz), 7.09 (1H, t, J=8.47 Hz), 6.81 (2H, m), 5.86 (1H, bs), 2.22 (3H, s) ppm.

$^{13}$C NMR (CD$_2$Cl$_2$, 100 MHz): 164.18, 163.29, 161.36, 143.03, 142.95, 142.86, 141.21, 134.34, 132.43, 132.37, 129.31, 128.44, 127.22, 126.95, 118.42, 117.52, 117.38, 114.02 (d, J=2.93 Hz), 105.10, 104.89, 14.12 (d, J=3.24 Hz) ppm.

Step 2: Synthesis of N4,N4"-di([1,1'-biphenyl]-4-yl)-N4,N4"-bis(3-fluoro-4-methylphenyl)-[1,1':4',1"-terphenyl]-4,4"-diamine 4,4"-Dibromo-1,1':4',1"-terphenyl (7.33 g, 18.9 mmol), N-(3-Fluoro-4-methylphenyl)-[1,1'-biphenyl]-4-amine (11.0 g, 39.7 mmol, 2.16 eq.), Pd(dba)$_2$ (217 mg, 0.57 mmol, 2.0 mol %), PtBu$_3$ (115 mg, 0.57 mmol, 2.0 mol %), and KOtBu (6.36 g, 56.7 mmol, 3.0 eq.), were charged in a flask under nitrogen atmosphere. The solids were suspended in anhydrous toluene, and the suspension was refluxed for 22 h at 80° C. After cooling to room temperature, it was filtered over silica, the pad was abundantly rinsed with tetrahydrofuran, and the filtrate was evaporated to dryness. The resulting solid was triturated in refluxing methanol (150 mL) for 20 min, and the suspension filtered hot, yielding after drying 14.9 g of the title compound (98.9% yield) with 98.92% purity according to HPLC. The product was then sublimed to yield yellow amorphous solid with 99.51% purity according to HPLC.

Elemental analysis: C 85.88% (86.13% theor.), H 5.60% (5.42% theor.) N 3.61% (3.59% theor.)

Glass Transition Onset: Tg=114° C. (from DSC 10 K/min), no melting peak observed.

DEVICE EXAMPLES

Comparative Example 1

The active OLED display according to previous art was prepared on a glass substrate provided with transparent ITO anode (thickness 90 nm), by subsequent vacuum deposition of following layers: p-doped HTL (10 nm, HT1 doped with 8 wt. % PD2); EBL (HT1, 120 nm); fluorescent EML (ABH113:NUBD370 from SFC Co. Ltd., Korea, 20 nm, 97:3 wt. %,); ETL (ET1:LiQ, 36 nm, 50:50 wt. %); and cathode (aluminium, 100 nm). The obtained results are given in Table 2, line 1.

Working Example 1

The comparative example 1 was reproduced with p-doped HTL made of HT2 doped with 3 wt. % PD2. The obtained results are given in Table 2, line 2.

Working Example 2

Working example 1 was reproduced using HT3 instead of HT2. The obtained results are given in Table 2, line 3.

Working Example 3

Comparative example 1 was reproduced with p-doped HTL made of HT4 doped with 7 wt. % PD2. The obtained results are given in Table 2, line 4.

Comparative Example 2

Working examples 1 and 2 were reproduced using HT1 instead of HT2 or HT3. The obtained results are given in Table 2, line 5.

TABLE 1

| Compound | Structure |
| --- | --- |
| HT1<br>N,N'-Di-1-naphthalenyl-N,N'-diphenyl-[1,1':4',1"-terphenyl]-4,4"-diamine<br>(CAS 139255-16-6) | 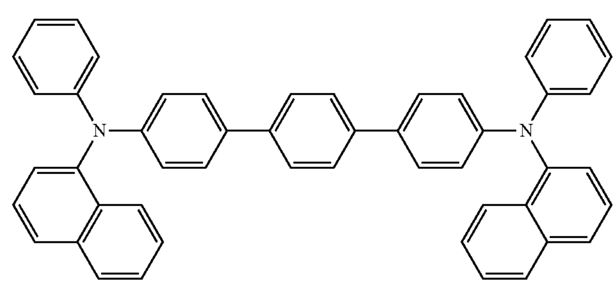 [SMILES: c1ccc(N(c2ccc(-c3ccc(-c4ccc(N(c5ccccc5)c5cccc6ccccc56)cc4)cc3)cc2)c2cccc3ccccc23)cc1] |

TABLE 1-continued
| Compound | Structure |
|---|---|
| HT2<br>N3,N5-di([1,1'-biphenyl]-4-yl)-N3,N5-bis(4-(tert-butyl)phenyl)-3'-(trifluoromethyl)-[1,1'-biphenyl]-3,5-diamine<br>(CAS 1602531-85-0) | 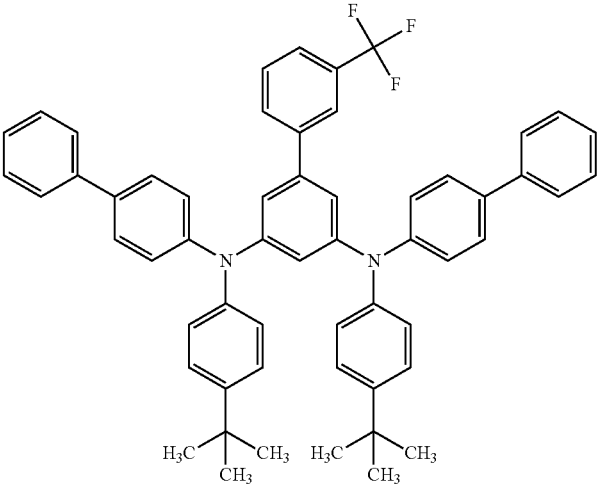 [SMILES: CC(C)(C)c1ccc(N(c2ccc(-c3ccccc3)cc2)c2cc(-c3cccc(C(F)(F)F)c3)cc(N(c3ccc(-c4ccccc4)cc3)c3ccc(C(C)(C)C)cc3)c2)cc1] |
| HT3<br>N4,N4''-di([1,1'-biphenyl]-4-yl)-N4,N4''-bis(3-fluoro-4-methylphenyl)-[1,1':4',1''-terphenyl]-4,4''-diamine | 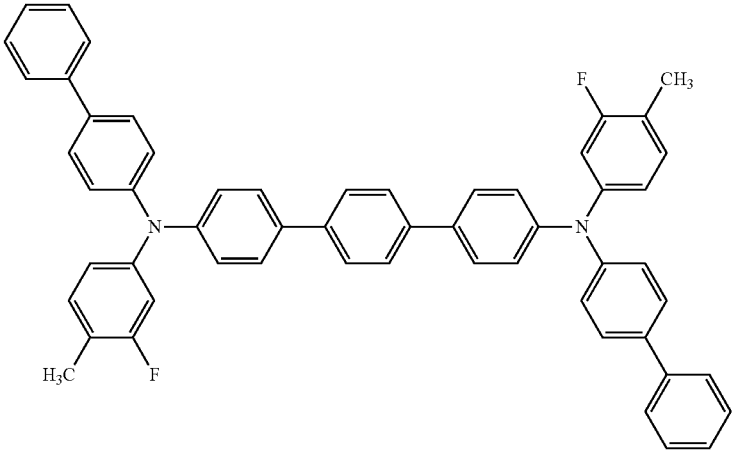 [SMILES: Cc1ccc(N(c2ccc(-c3ccccc3)cc2)c2ccc(-c3ccc(-c4ccc(N(c5ccc(-c6ccccc6)cc5)c5ccc(C)c(F)c5)cc4)cc3)cc2)cc1F] |
| HT4<br>N3,N3'-bis([1,1'-biphenyl]-4-yl)-N3,N3'-diphenyl-[1,1'-biphenyl]-3,3'-diamine<br>(CAS 1242056-42-3) | 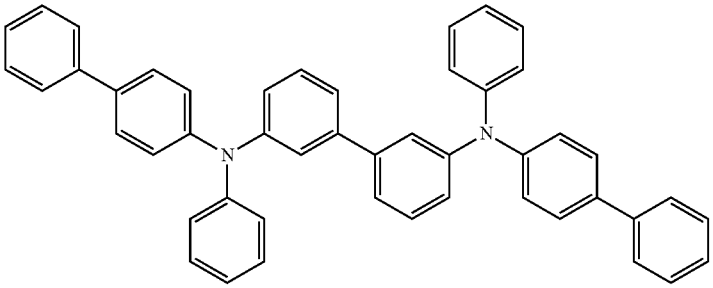 [SMILES: c1ccc(-c2ccc(N(c3ccccc3)c3cccc(-c4cccc(N(c5ccccc5)c5ccc(-c6ccccc6)cc5)c4)c3)cc2)cc1] |

TABLE 1-continued

| Compound | Structure |
|---|---|
| PD2<br>2,2',2''-(cyclopropane-1,2,3-triylidene)-tris[2-(4-cyanoperfluorophenyl)-acetonitrile] (CAS 1224447-88-4) | 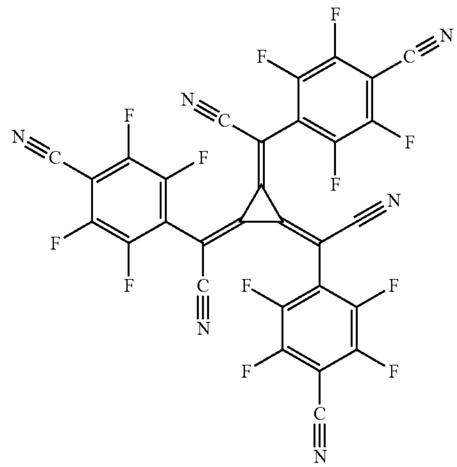 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F] |
| ET1<br>2-(4-(9,10-Di(naphthalen-2-yl)anthracen-2-yl)phenyl)-1-phenyl-1H-benzo[d]imidazole<br>(CAS 561064-11-7) | 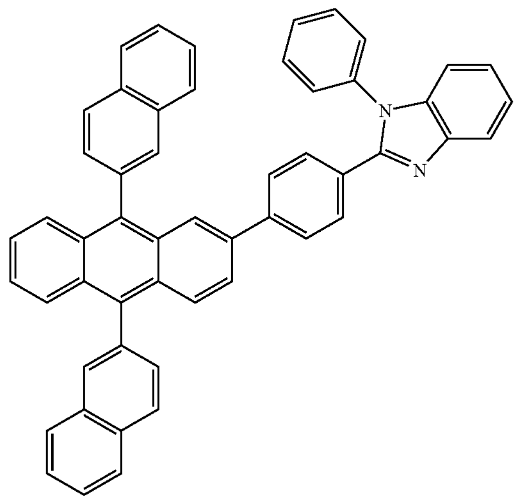 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] |
| LiQ<br>8-Hydroxyquinolato lithium<br>(CAS 850918-68-2) | 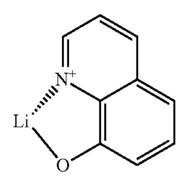 |

TABLE 2

| HTM1 (HTL) | HOMO (eV) | $\mu 0$ [$10^{-7}$ cm$^2$/Vs] | HTL conductivity [$10^{-6}$ S/m] | HTL p-dopant concentration (wt. %) | HOMO EBL (eV) | Voltage at 15 mA/cm$^2$ [V] | QE at 15 mA/cm$^2$ % | LT97 at 15 mA/cm$^2$ h | Voltage rise at 15 mA/cm$^2$ |
|---|---|---|---|---|---|---|---|---|---|
| HT1 | −5.25 | 7180 | 7630 | 8 | −5.25 | 4.230 | 6.29 | 46 | No |
| HT2 | −5.20 | 2.32 | 4.71 | 3 | −5.25 | 4.290 | 6.49 | 40 | No |
| HT3 | −5.28 | 2520 | 165 | 3 | −5.25 | 4.139 | 6.36 | 55 | No |
| HT4 | −5.33 | 2.32 | 60 | 7 | −5.25 | 4.30 | 6.40 | 40 | No |
| HT1 | −5.25 | 7180 | 177 | 3 | −5.25 | 4.493 | 6.50 | — | yes |

Following, with regard to terms used in Table 2, further explanation is provided.

The term "HOMO" refers to the Highest Occupied Molecular Orbital energy level derived from cyclic voltammetry of molecules in solution and expressed in the physical absolute scale against vacuum taken as zero energy level. The given HOMO levels were calculated from redox potential $V_{cv}$ (measured by cyclic voltammetry (CV) as specified below and expressed in the scale taking the potential of standard redox pair ferricenium/ferrocene (Fc$^+$/Fc) equal zero) according to equation $E_{HOMO} = -q^* V_{cv} - 4.8$ eV, wherein q* stands for the charge of an electron (1e).

The redox potential can be determined by cyclic voltammetry, e.g. with a potentiostatic device Metrohm PGSTAT30 and software Metrohm Autolab GPES at room temperature. The redox potentials given at particular compounds was measured in an argon de-aerated, dry 0.1M THF (Tetrahydrofuran) solution of the tested substance, under argon atmosphere, with 0.1M tetrabutylammonium hexafluorophosphate supporting electrolyte, between platinum working electrodes and with an Ag/AgCl pseudo-standard electrode (Metrohm Silver rod electrode), consisting of a silver wire covered by silver chloride and immersed directly in the measured solution, with a scan rate of 100 mV/s. In the measurement, the first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard Fc+/Fc redox couple, afforded finally the values reported above. All studied compounds as well as the reported comparative compounds showed well-defined reversible electrochemical behavior. Alternatively, dichloromethane can be used as solvent.

A simple rule is very often used for the conversion of redox potentials into electron affinities (EA) and ionization potential (IP): IP (in eV)=4.84 eV+e*Eox (wherein Eox is given in Volt vs. ferrocene/ferrocenium (Fc/Fc+) and EA (in eV)=4.84 eV+e*Ered (Ered is given in Volt vs. Fc/Fc+), respectively (see B. W. D'Andrade, Org. Electron. 6, 11-20 (2005)), e* is the elemental charge. It is common practice, even if not exactly correct, to use the terms "energy of the HOMO" E(HOMO) and "energy of the LUMO" E(LUMO), respectively, as synonyms for the ionization energy and electron affinity (Koopmans Theorem).

The term "µ0" refers to zero field mobility. Mobility is determined in admittance spectroscopy from capacitance vs. frequency tracks and is described in detail in reference: Nguyen et al., Determination of charge-carrier transport in organic devices by admittance spectroscopy: Application to hole mobility in α-NPD." Physical Review B 75.7 (2007): 075307.

The devices used for the hole mobility measurement had a layer structure of ITO (100 nm)/HT1:PD2 (10 nm)/assessed HTM (700 nm)/ HT1:PD2 (10 nm)/Au (10 nm)/Al 100 nm). The 10 nm hole injecting layers of HT1:PD2 (weight ratio 90:10) were provided to ensure ohmic contacts to the ITO anode and Au/Al cathode. Measurement of geometric capacitance was done by using a sample as given above without HILs. The following conditions and parameters applied: room temperature, amplitude: 20 mV, frequency: 110 Hz to 2 MHz. The voltage range was chosen appropriately, to allow the mobility estimation at relevant current densities in the range from 10 to 50 mA/cm$^2$.

The column "conductivity" refers to electrical conductivity measured by standard four point method described e.g. in WO 2013/135237 A1, on a thin film of the chosen matrix comprising the PD2 dopant in concentration given in the next column of the Table 2. The films prepared for conductivity measurements were vacuum deposited onto glass substrate covered with ITO contacts; the conductivities were estimated at room temperature.

QE stands for quantum efficiency; LT97 stands for the timespan within the luminance of the device operated at given current density had not changed more than 3% of its initial value. "Voltage rise" is another important operational characteristic of OLEDs. In stable devices operated at constant current, the voltage remains constant. Should the voltage in a testing device raise more than 5% of its initial value during the desired lifetime, it is a sign that the tested material makes the device instable.

FIGS. 2 to 5 show that OLEDs proposed here allow for suppressed crosstalk in displays, have the same performance as previous art OLED of Comparative example 1 that comprises the redox-doped HTL with significantly higher conductivity than HTLs of Working examples 1 to 3. It is supposed that displays of the present disclosure show suppressed crosstalk due to redox-doped electrically doped hole transport layer having sufficient dopant concentration, still allowing good stability of the device and good charge injection from the anode and/or into the adjacent organic layer, but having significantly lower conductivity due to low charge carrier mobility and/or low actual charge carrier concentration.

An attempt to decrease the conductivity in a state-of-the-art OLED comprising the HT1 matrix with hole mobility above $5.10^{-4}$ cm$^2$/Vs, as done in the Comparative example 2, resulted in a device lacking the necessary operational stability. These results surprisingly showed that sufficient concentration of a redox p-dopant is important not only for retaining good voltage, but also for the device stability. It was furthermore demonstrated that despite low conductivity of HTLs comprising matrices having low hole mobilities (below $5.10^{-4}$ cm$^2$/Vs), in combination with a redox p-dopant, these matrices surprisingly allow construction of OLEDs having equal or better voltages and other performance parameters as the state-of-the-art devices comprising high-conductivity HTL, with the substantial advantage that the inventive OLEDs suppress the pixel crosstalk significantly, thanks to their low conductivity HTL, if used as pixels in state-of-the-art displays comprising a common HTL shared by plurality of pixels.

The features disclosed in the foregoing description and in the claims may, both separately and in any combination thereof, be material for realizing the aspects of the disclosure in diverse forms thereof.

Key symbols and abbreviations used throughout the application:
CV cyclic voltammetry
DSC differential scanning calorimetry
EBL electron blocking layer
EIL electron injecting layer
EML emitting layer
eq. equivalent
ETL electron transport layer
ETM electron transport matrix
Fc ferrocene
Fc⁻ ferricenium
HBL hole blocking layer
HIL hole injecting layer
HOMO highest occupied molecular orbital HPLC high performance liquid chromatography
HTL hole transport layer
p-HTL p-doped hole transport layer
HTM hole transport matrix
ITO indium tin oxide
LUMO lowest unoccupied molecular orbital
mol. % molar percent
NMR nuclear magnetic resonance
OLED organic light emitting diode
OPV organic photovoltaics
QE quantum efficiency
$R_f$ retardation factor in TLC
RGB red-green-blue
TCO transparent conductive oxide
TFT thin film transistor
$T_g$ glass transition temperature
TLC thin layer chromatography
wt. % weight percent

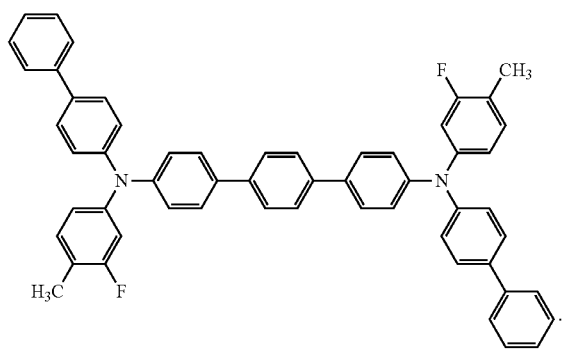 [SMILES: Cc1ccc(N(c2ccc(-c3ccccc3)cc2)c2ccc(-c3ccc(-c4ccc(N(c5ccc(-c6ccccc6)cc5)c5ccc(C)c(F)c5)cc4)cc3)cc2)cc1F]

The invention claimed is:

1. An active OLED display, comprising
a plurality of OLED pixels, each of the OLED pixels comprising an anode, a cathode, and a stack of organic layers, wherein the stack of organic layers
is provided between and in contact with the cathode and the anode, and
comprises an electron transport layer, a hole transport layer, and a light emitting layer provided between the hole transport layer and the electron transport layer, and
a driving circuit configured for separately driving the pixels of the plurality of OLED pixels,
wherein, for the plurality of OLED pixels, a common hole transport layer is formed by the hole transport layers provided in the stack of organic layers of the plurality of OLED pixels, the common hole transport layer comprising a hole transport matrix material and an electrical p-dopant, and wherein the electrical conductivity of the common hole transport layer is lower than $1 \times 10^{-3}$ S·m$^{-1}$ and higher than $1 \times 10^{-8}$ S·m$^{-1}$, and
wherein the common hole transport layer has a thickness of less than 50 nm.

2. The active OLED display according to claim 1, wherein the LUMO energy level of the electrical p-dopant, expressed in the absolute scale referring to vacuum energy level being zero, is at least 150 meV higher than the highest HOMO energy level of the one or more compounds forming the hole transport matrix material.

3. The active OLED display according to claim 1, wherein the LUMO energy level of the electrical p-dopant, expressed in the absolute scale referring to vacuum energy level being zero, is less than 600 meV above the highest HOMO energy level of the one or more compounds forming the hole transport matrix material.

4. The active OLED display according to claim 1, wherein the hole transport matrix material consists of one or more compounds having energies of their highest occupied molecular orbitals, expressed in the absolute scale referring to vacuum energy level being zero, in the range from −4.8 eV to −5.5 eV.

5. The active OLED display according to claim 1, wherein the common hole transport layer has a thickness of more than 3 nm.

6. The active OLED display according to claim 1, wherein the work function of the anode, expressed in the absolute scale referring to vacuum energy level being zero, is less than 500 meV above the highest LUMO energy level of the one or more compounds forming the p-dopant.

7. The active OLED display according to claim 1, wherein the stack of organic layers further comprises an electron blocking layer provided between the hole transport layer and the light emitting layer.

8. The active OLED display according to claim 7, wherein the electron blocking layer has a thickness of more than 30 nm.

9. The active OLED display according to claim 7, wherein the electron blocking layer has a thickness of less than 200 nm.

10. The active OLED display according to claim 7, wherein each of the one or more compounds forming the electron blocking layer has a HOMO level, expressed in the absolute scale referring to vacuum energy level being zero, higher than the HOMO level of any compound forming the hole transport matrix material of the common hole transport layer.

11. The active OLED display according to claim 7, wherein the hole transport matrix material of the common hole transport layer is provided with a hole mobility which is lower than a hole mobility of a matrix material of the electron blocking layer.

12. The active OLED display according to claim 1, wherein the hole transport matrix material of the common hole transport layer is selected from one or more compounds comprising a conjugated system of delocalized electrons, the conjugated system comprising lone electron pairs of at least two tertiary amine nitrogen atoms.

13. The active OLED display according to claim 1, wherein the light emitting layer comprises a plurality of separated sub-regions, each of the sub-regions being assigned to one of the pixels from the plurality of OLED pixels.

14. The active OLED display according to claim 1, wherein, for the plurality of OLED pixels, a common electron transport layer is formed by the electron transport layers provided in the stack of organic layers of the plurality of OLED pixels.

15. The active OLED display according to claim 14, wherein the common electron transport layer comprises an electron transport matrix material and an electrical n-dopant.

16. A method of operating an active OLED display having a plurality of OLED pixels according claim 1, wherein a driving circuit applies a driving current to each pixel of the plurality of OLED pixels, the driving current being different for neighbor OLED pixels at an operation time.

17. Compound having formula